United States Patent
Orge et al.

(10) Patent No.: US 10,970,921 B2
(45) Date of Patent: Apr. 6, 2021

(54) APPARATUS AND METHOD FOR CONSTRUCTING A VIRTUAL 3D MODEL FROM A 2D ULTRASOUND VIDEO

(71) Applicant: University Hospitals Cleveland Medical Center, Cleveland, OH (US)

(72) Inventors: Faruk Halim Orge, Solon, OH (US); Richard Ward Helms, Cleveland, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 0 days.

(21) Appl. No.: 16/337,776

(22) PCT Filed: Sep. 28, 2017

(86) PCT No.: PCT/US2017/053870
§ 371 (c)(1),
(2) Date: Mar. 28, 2019

(87) PCT Pub. No.: WO2018/064248
PCT Pub. Date: Apr. 5, 2018

(65) Prior Publication Data
US 2020/0005528 A1 Jan. 2, 2020

Related U.S. Application Data

(60) Provisional application No. 62/401,952, filed on Sep. 30, 2016.

(51) Int. Cl.
*G06T 17/00* (2006.01)
*G06T 5/20* (2006.01)
(Continued)

(52) U.S. Cl.
CPC ............... *G06T 17/00* (2013.01); *A61B 8/10* (2013.01); *A61B 8/5207* (2013.01);
(Continued)

(58) Field of Classification Search
CPC ........... G06T 17/00; G06T 15/08; G06T 5/20; G06T 5/002; G06T 3/0006;
(Continued)

(56) References Cited

U.S. PATENT DOCUMENTS

| | | | |
|---|---|---|---|
| 4,831,528 A | 5/1989 | Crawford et al. | |
| 5,159,931 A | 11/1992 | Pini | |

(Continued)

FOREIGN PATENT DOCUMENTS

| | | |
|---|---|---|
| CN | 201379592 Y | 1/2010 |
| EP | 0844496 A2 | 5/1998 |
| WO | 2014099825 A2 | 6/2014 |

OTHER PUBLICATIONS

International Search Report and Written Opinion for PCT/US2017/053870, dated Nov. 30, 2017, 13 pages.
(Continued)

*Primary Examiner* — Tapas Mazumder
(74) *Attorney, Agent, or Firm* — Pearne & Gordon LLP

(57) ABSTRACT

A method for creating a three-dimensional image of an object from a two-dimensional ultrasound video is provided. The method includes acquiring a plurality of two-dimensional ultrasound images of the object and recording a plurality of videos based on the acquired two-dimensional ultrasound images. Each of the videos includes a plurality of frames. The method further includes separating each of the plurality of frames, cropping each of the plurality of frames to isolate structures intended to be reconstructed, selecting a frame near a center of the object and rotating the image to create a main horizontal landmark, and aligning each frame
(Continued)

Target image

Misaligned image

Rotation →

Translation →

Registered image to the main horizontal landmark. The method also includes removing inter-frame jitter by aligning each of the plurality of frames relative to a previous frame of the plurality of frames, reducing the noise of each of the frames, and stacking each of the frames into a three-dimensional volume.

18 Claims, 6 Drawing Sheets

(51) Int. Cl.
    *A61B 8/10*     (2006.01)
    *A61B 8/08*     (2006.01)
    *G06T 3/00*     (2006.01)
    *G06T 5/00*     (2006.01)
    *G06T 15/08*     (2011.01)

(52) U.S. Cl.
    CPC .......... *A61B 8/5269* (2013.01); *G06T 3/0006* (2013.01); *G06T 5/002* (2013.01); *G06T 5/20* (2013.01); *G06T 15/08* (2013.01); *G06T 2200/08* (2013.01); *G06T 2207/10016* (2013.01); *G06T 2207/10132* (2013.01); *G06T 2207/20032* (2013.01); *G06T 2207/30041* (2013.01); *G06T 2210/22* (2013.01); *G06T 2210/41* (2013.01); *G06T 2215/16* (2013.01)

(58) Field of Classification Search
    CPC ............. G06T 2215/16; G06T 2210/41; G06T 2210/22; G06T 2207/30041; G06T 2207/20032; G06T 2207/10132; G06T 2207/10016; G06T 2200/08; G06T 7/33; A61B 8/5269; A61B 8/5207; A61B 8/10; A61B 8/466; A61B 8/14; A61B 8/08
    See application file for complete search history.

(56) References Cited

U.S. PATENT DOCUMENTS

| | | | |
|---|---|---|---|
| 5,353,354 A | 10/1994 | Keller et al. | |
| 5,396,890 A | 3/1995 | Weng | |
| 5,454,371 A | 10/1995 | Fenster et al. | |
| 5,540,229 A | 7/1996 | Collet-Billon et al. | |
| 5,562,095 A | 10/1996 | Downey et al. | |
| 5,842,473 A | 12/1998 | Fenster et al. | |
| 5,860,924 A | 1/1999 | Quistgaard | |
| 5,872,571 A | 2/1999 | Arling | |
| 6,059,727 A | 5/2000 | Fowlkes et al. | |
| 6,106,471 A | 8/2000 | Wiesauer et al. | |
| 6,262,740 B1 * | 7/2001 | Lauer .................. | G06T 1/60 345/424 |
| 6,342,891 B1 | 1/2002 | Fenster et al. | |
| 6,390,982 B1 | 5/2002 | Bova et al. | |
| 6,511,426 B1 | 1/2003 | Hossack et al. | |
| 6,544,178 B1 | 4/2003 | Grenon et al. | |
| 6,688,177 B2 | 2/2004 | Wiesauer | |
| 6,723,050 B2 | 4/2004 | Dow et al. | |
| 6,755,787 B2 | 6/2004 | Hossack et al. | |
| 6,825,838 B2 | 11/2004 | Smith et al. | |
| 6,939,301 B2 | 9/2005 | Abdelhak et al. | |
| 6,949,071 B1 | 9/2005 | Saied et al. | |
| 6,988,899 B2 | 1/2006 | Vafi et al. | |
| 7,366,992 B2 | 4/2008 | Thomas, III et al. | |
| 7,457,457 B2 | 11/2008 | Ives et al. | |
| 7,480,398 B2 | 1/2009 | Kleen et al. | |
| 9,179,890 B2 | 11/2015 | Ionasec et al. | |
| 2002/0068863 A1 | 6/2002 | Slack | |
| 2002/0133075 A1 | 9/2002 | Abdelhak | |
| 2003/0097068 A1 * | 5/2003 | Hossack .............. | A61B 8/5276 600/443 |
| 2006/0098864 A1 | 5/2006 | Ziel | |
| 2008/0175453 A1 | 7/2008 | Hao et al. | |
| 2009/0156933 A1 | 6/2009 | Gerard et al. | |
| 2009/0306509 A1 | 12/2009 | Pederson et al. | |
| 2012/0237102 A1 | 9/2012 | Savitsky et al. | |
| 2015/0051489 A1 * | 2/2015 | Caluser ................ | A61B 8/4254 600/440 |

OTHER PUBLICATIONS

Extended European Search Report for European Application No. 17857379.6 dated Apr. 2, 2020.

* cited by examiner

APPARATUS AND METHOD FOR CONSTRUCTING A VIRTUAL 3D MODEL FROM A 2D ULTRASOUND VIDEO

CROSS-REFERENCES TO RELATED APPLICATIONS

This application claims the benefit of U.S. Provisional Patent Application Ser. No. 62/401,952 entitled "APPARATUS AND METHOD FOR CONSTRUCTING A VIRTUAL 3D MODEL FROM A 2D ULTRASOUND VIDEO" which was filed Sep. 30, 2016. The entirety of the aforementioned application is herein incorporated by reference.

BACKGROUND

Ultrasonic imaging is a popular technique in medicine used to create visual representations of the interior of a body for clinical analysis and medical intervention. However, the scan provides either two-dimensional images or a video and no easy way to filter out noise, which confines the accuracy of the analysis.

Ultrasonography is used routinely in ophthalmic examination to evaluate structures in the eye, to rule out pathology and follow certain pathologic and physiologic changes in the eye. The scan, however, provides a two-dimensional image which somewhat limits the detailed evaluation of the tissues. By converting the two-dimensional media into a three-dimensional model, it is easier to see the contours and fine details of the tissue without having to mentally approximate frame by frame. This allows the user to understand, and helps recognizing, subtle problems which would be otherwise missed.

Currently, few methods and apparatuses achieve such three-dimensional models and are rarely used in the ophthalmology field.

SUMMARY

The following presents a simplified summary of the invention in order to provide a basic understanding of some example aspects of the invention. This summary is not an extensive overview of the invention. Moreover, this summary is not intended to identify critical elements of the invention or to delineate the scope of the invention. The sole purpose of the summary is to present some concepts in a simplified form as a prelude to the more detailed description that is presented later.

Provided are a plurality of example embodiments, including, but not limited to methods and devices for creating a three-dimensional image of a body part, such as the eye, for example, in order to diagnose problems and determine solutions.

In one general aspect, a method for creating a three-dimensional image of an object from a two-dimensional ultrasound video is provided. The method includes acquiring a plurality of two-dimensional ultrasound images of the object and recording a plurality of videos based on the acquired two-dimensional ultrasound images. Each of the plurality of videos comprises a plurality of frames. The method further includes separating each of the plurality of frames and cropping each of the plurality of frames to isolate structures intended to be reconstructed. The method also includes selecting a frame near a center of the object and rotating the image to create a main horizontal landmark. The method further includes aligning each of the plurality of frames to the main horizontal landmark. The method also includes stacking each of the aligned plurality of frames into a three-dimensional volume.

In another general aspect, the method for creating a three-dimensional image of an object from a two-dimensional ultrasound video includes removing inter-frame jitter by aligning each of the plurality of frames relative to a previous frame of the plurality of frames.

In another general aspect, the method for creating a three-dimensional image of an object from a two-dimensional ultrasound video includes reducing a noise of each of the plurality of frames.

In another general aspect, the object is a part of a human body.

In another general aspect, the object is a human eye.

In another general aspect, the plurality of two-dimensional ultrasound images are B-scan images of the human eye.

In another general aspect, the acquiring a plurality of two-dimensional ultrasound images is performed by a Quantel ultrasonic biomicroscope or a B-scan probe.

In another general aspect, each of the plurality of frames represents an individual slice of a particular segment of one of the two-dimensional ultrasound images in one dimension.

In another general aspect, the cropping each of the plurality of frames comprises excluding extraneous parts of the images.

In another general aspect, the selecting the frame near the center of the object and rotating the image rotates all other frames by the same amount.

In another general aspect, the reducing a noise of each of the plurality of frames comprises low-pass filtering or median filtering.

In another general aspect, the stacking each of the plurality of frames with reduced noise into a three-dimensional volume comprises removing layers of the three-dimensional image.

In another general aspect, the removing of layers of the three-dimensional image is performed by using planes to exclude voxels outside of a cuboidal region specified by a user.

In one general aspect, a method for creating a three-dimensional image of an object from a two-dimensional ultrasound video is provided. The method includes obtaining a plurality of two-dimensional ultrasound video images of the object. Each of the plurality of two-dimensional ultrasound video images comprises a plurality of individual frames. The method further includes isolating each of the plurality of individual frames from each of the plurality of two-dimensional ultrasound video images. The method also includes individually processing each of the plurality of individual frames to improve their suitability for conversion. The method further includes assembling together the individually processed plurality of individual frames to create the three-dimensional image of the object.

In another general aspect, the assembling together the individually processed plurality of individual frames uses landmarks that identify common areas in the individually processed plurality of individual frames.

In another general aspect, the assembling together the individually processed plurality of individual frames aligns each of the individually processed plurality of individual frames based on image boundaries in adjacent frames of the individually processed plurality of individual frames.

In another general aspect, the individually processing each of the plurality of individual frames comprises selecting an individual frame near a center of the object and rotating the individual frame to create a main horizontal landmark.

In another general aspect, the assembling together the individually processed plurality of individual frames aligns each of the individually processed plurality of individual frames based on the main horizontal landmark.

In another general aspect, the assembling together the individually processed plurality of individual frames comprises creating an object that contains a three-dimensional array of values corresponding to slices, rows, and columns, wherein the slices are enumerated from top to bottom, the rows from back to front, and the columns from left to right. The assembling together the individually processed plurality of individual frames further comprises visualizing the three-dimensional image of the object by using volume rendering that displays a projection of discretely sampled three-dimensional data values, wherein each volume element is represented by a single value or a list of values. The assembling together the individually processed plurality of individual frames also comprises outputting a three-dimensional image format as a picture of a projection of the image.

Other features and aspects may be apparent from the following detailed description, the drawings, and the claims.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

Figure 1:
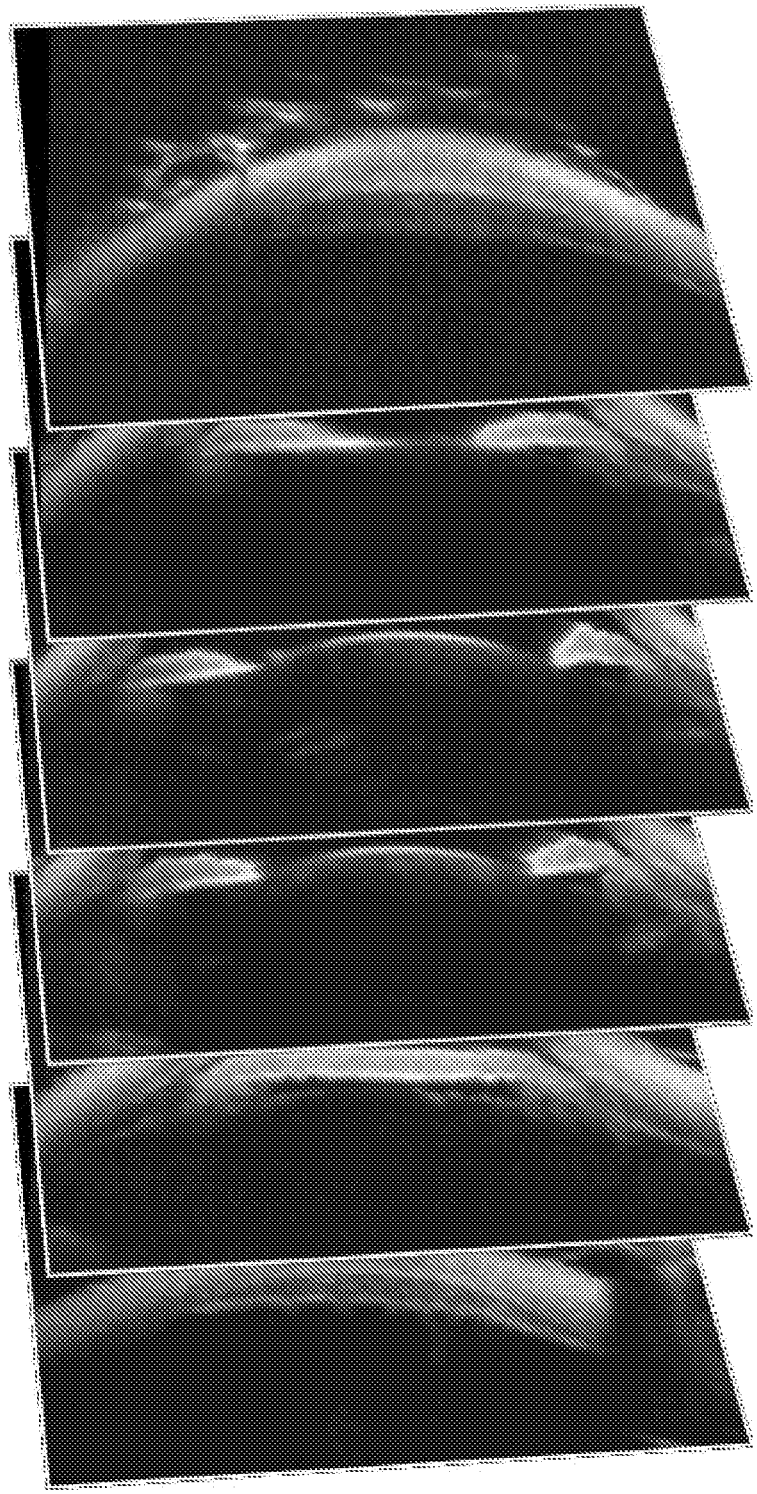
FIG. 1 is a schematic view of individual frames, which represent individual slices in one dimension of two dimensional video images.

Throughout the drawings and the detailed description, unless otherwise described, the same drawing reference numerals will be understood to refer to the same elements, features, and structures. The relative size and depiction of these elements may be exaggerated for clarity, illustration, and convenience.

The figures show various aspects of embodiments of the invention, as described in more detail hereinbelow.

DETAILED DESCRIPTION

Example embodiments that incorporate one or more aspects of the apparatus and methodology are described and illustrated in the drawings. These illustrated examples are not intended to be a limitation on the present disclosure. For example, one or more aspects of the disclosed embodiments can be utilized in other embodiments and even other types of devices. Moreover, certain terminology is used herein for convenience only and is not to be taken as a limitation.

The method described herein relates to conversion of two dimensional (2D) video images into a virtual three-dimensional (3D) object which can be analyzed and manipulated. The method described herein utilizes ultrasound videos of the eye. However, even though the primary focus of this description uses ultrasounds of the eye, it should be applicable to all ultrasound images of different body structures.

The described method involves reconstructing images of multiple slices of the eye, similar to a CT scan three-dimensional (3D) reconstruction, to create an improved 3D image that provides a much needed overview of the ocular structures. The 3D image can be helpful in identifying anatomical structures quickly and diagnosing pathologies with greater accuracy.

3D reconstruction of the full anterior chamber can be used for automatic measurement of clinically relevant parameters. One example is the iridocorneal angle which has implications for aqueous outflow and diseases such as glaucoma. 3D imaging allows 360-degree measurement of the angle at one time, in contrast to most other techniques which measure the angle in a single plane or a fixed number of locations. Furthermore, measurement of the angle from a 3D volume is less prone to errors caused by oblique sampling planes.

3D reconstruction also allows measuring the anterior chamber (AC) volume and height. The AC volume is usually measured by a geometric approximation which does not take into account the proper curvature of the iris or the variation around the optic axis. 3D reconstruction enables automatic segmentation of the entire AC with the associated measurements at voxel-level accuracy.

Generally, the method utilizes a plurality of two dimensional ultrasound images (i.e., B-scan images) taken of a human organ, such as the eye, in a traditional or improved manner. With respect to eye images, these images are typically performed in a linear slicing mode which shows only a single particular segment of the eye. First, the 2D image slices are processed in order to improve their suitability for conversion.

After that, the processed images are "assembled" together to create a 3D image from the original 2D images to better represent the actual physical construction of the organ in order to show various structures, including damage, defects, or other items of interest, which can greatly improve ultrasonography in ophthalmology. All image analyses and manipulations can be done using a system such as the Matlab® commercial package, Mathematica, ImageJ, some other commercial package, or using customized software.

The image assembly process is aided by information provided in the images themselves, such as "landmarks" that identify common areas in the different images, or by using image boundaries in adjacent images to aid in such reconstruction of the actual organ in 3D from the series of 2D images. Commercially available software, open source software, and/or customized software can be used to implement the process, which could also utilize various manual steps as alternatives as well. However, at least one or more of the steps of the method cannot be performed manually. In addition, the creation of the 3D images permits obtaining volumetric measurements and calculations about the imaged organ(s).

Furthermore, the process is improved by using a new machine to help automate the scanning process using various commercial probes, as opposed to the current manual process, to ensure consistent images and aid in the reconstruction process.

Example Methodology

In an example method, the images of the desired body part (e.g., human eye) can be acquired with Quantel ultrasonic biomicroscope and with B-scan probe. A video of the acquired images may be recorded by the machine and can be translated into an Audio Video Interleaved ("AVI") format. The videos in an example embodiment can be 10 seconds long, and may include multiple individual frames of two dimensional imaging while the eye is scanned using an ultrasonic probe.

The videos are read in a movie, or a series of movies, and the frames, which represent individual slices in one dimension, are separated or isolated (as illustrated in FIG. 1).

Each frame is then cropped crudely, using video editing software, such as Pinnacle Studio 18 or ImageMagick, for example, to show just the area of interest, isolate the structures intended to be reconstructed, and to remove extraneous text and parts of the images, such as the blue frame and the patient name which are added by the manufacturer software.

Once the preparatory work for the video is done, for one example embodiment it is imported into a program encoded in the Matlab® commercial package, where it is then saved as a plurality of individual images.

Next, the individual images are processed prior to their conversion into a 3D image. Specifically, the user selects an individual frame near the center of the eye and rotates the image to make the iris (e.g., the main horizontal landmark) truly horizontal. This manipulation rotates all other individual frames by the same amount.

Figure 2:
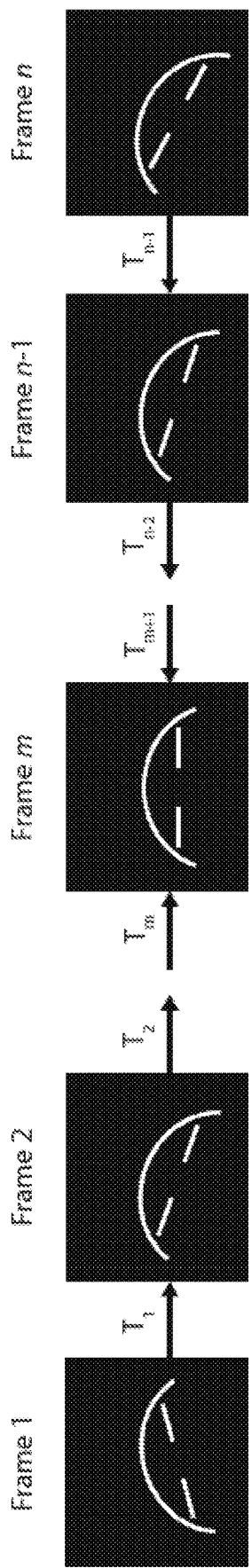
FIG. 2 is a schematic illustration of the selection of a frame among the individual frames near the center of the eye and the rotation of the image.
Figure 3:
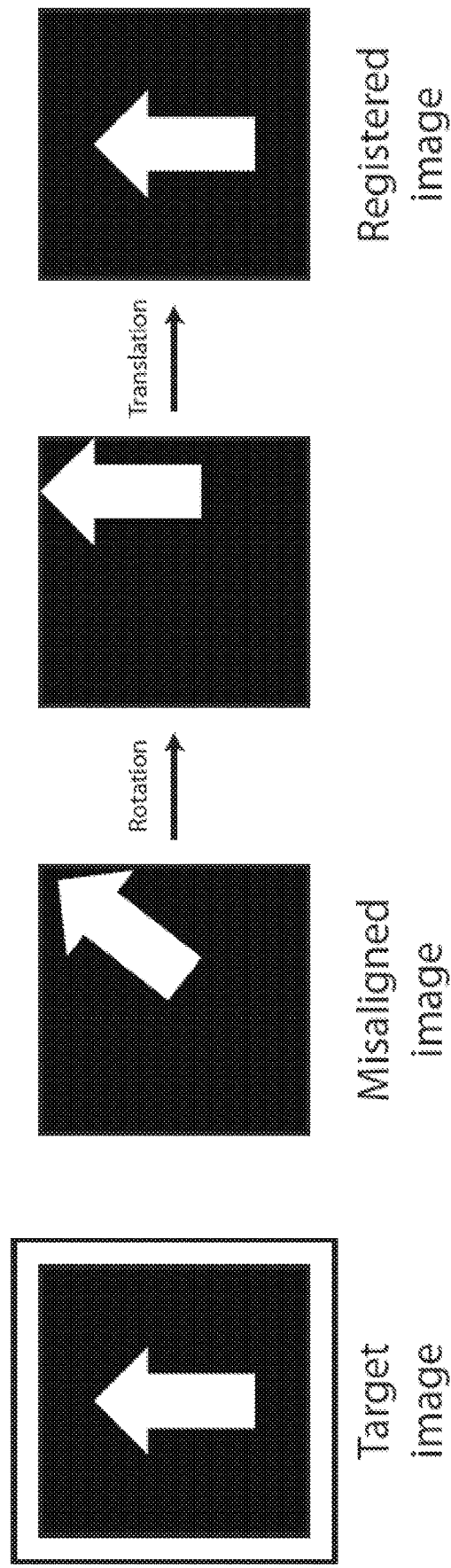
FIG. 3 is a schematic illustration of the registration of the individual frames relative to one another.

Next, the individual frames are registered relative to one another to remove inter-frame jitter. In laboratory conditions, jitter is basically absent. However, when moving the probe by hand or when the probe is used on a breathing patient, there is undesirable motion between the probe and the patient's eye. This results in jumps or waves in the 3D reconstruction. As show in FIG. 2, to remove these jumps or waves, the method aligns each individual frame to the one before it. Mathematically speaking, as show in FIG. 3, the transformation (which is usually restricted to translation or rotation) minimizes the numerical difference between pixels in adjacent individual frames.

As a next step, the images are de-noised. Specifically, the conditions under which the original individual frames were recorded can be noisy. There are hundreds of algorithms (or filters) that can be used to reduce this noise. Some of the more effective algorithms have been low-pass filtering and median filtering, for example.

After the 2D images are de-noised, they are stacked into a 3D volume that can be manipulated within custom software. For example, since the user typically desires to see structures inside the eye, it may be important to have the ability to remove layers of the 3D images. This removal is accomplished by simply using planes to exclude voxels outside of a cuboidal region that the user can specify.

Figure 4:
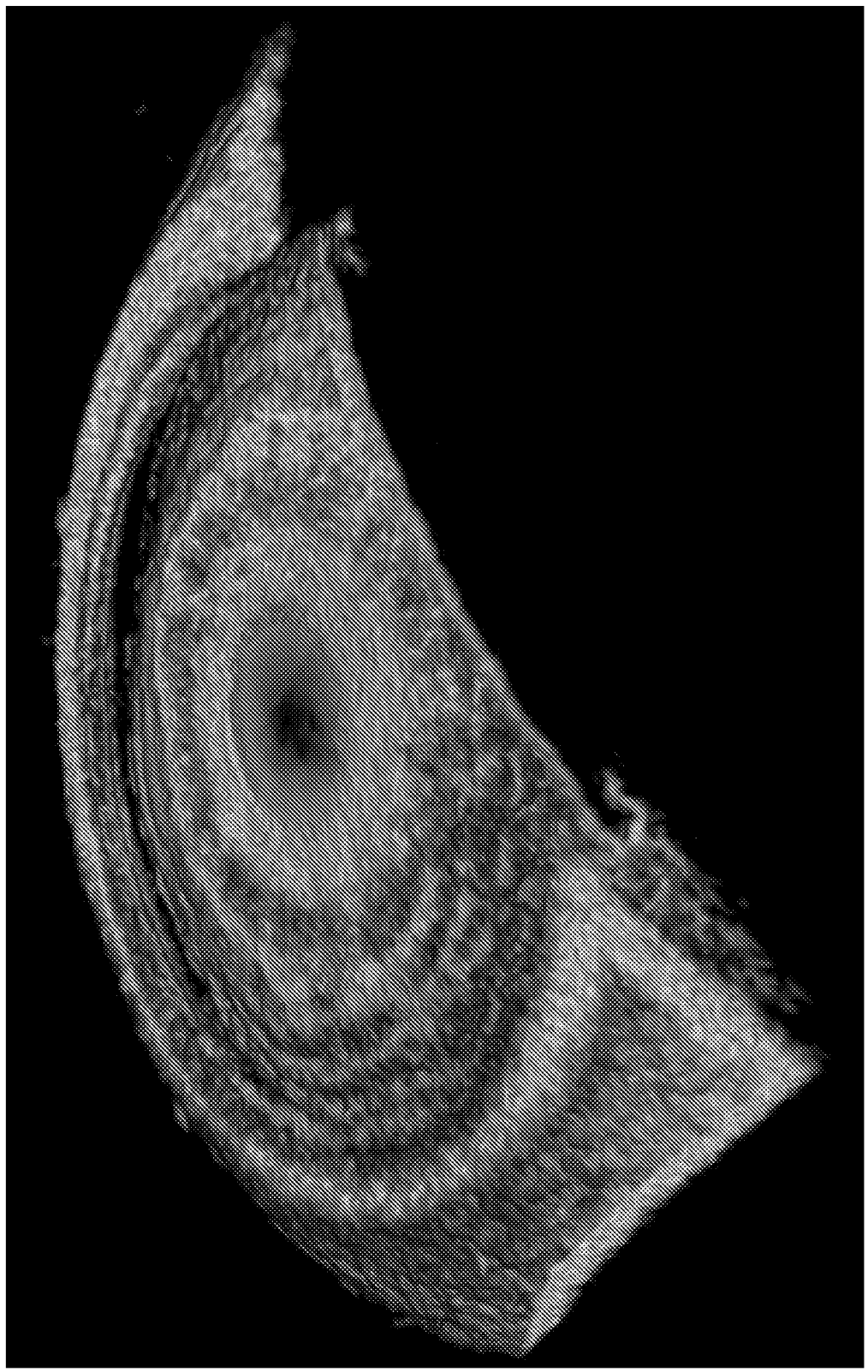
FIG. 4 is an image of a 3D reconstructed resulting model of an eye.

The conversion into 3D images is done by creating an object that contains a three-dimensional array of values (or lists of values) that represent a 3D raster image. The first three dimensions of the object correspond to slices, rows, and columns, respectively. Slices are enumerated from top to bottom, rows from back to front, and columns from left to right. Then a 3D object is visualized using a set of techniques collectively known as volume rendering that display a projection of discretely sampled 3D data values. Given an object containing a regular volumetric grid, each volume element is known as a voxel and is represented by a single value (or list of values). Upon output, a 3D image formats as a picture of a projection of the image (not as a 3D array of values). As shown in FIG. 4, a 3D model of an eye was successfully created from an ultrasound video of that eye. This is a significant achievement in a revolutionary diagnostic tool.

Example Apparatus and Control Software

A typical apparatus for obtaining a Cineloop video imaging of a B-scan ultrasonography generally includes an ultrasonic probe attached to a motor system. The motor system can help in arranging the speed and the direction of the Cineloop video imaging. However, an apparatus for obtaining a good quality Cineloop that also obtains images steadily and consistently at a set speed is a challenge and is difficult to achieve even by an experienced ultrasonographer or a surgeon with steady hands. Especially for a 3D reconstruction of a B-scan Cineloop, it is desirable to obtain a steady, reproducible, and reliable Cineloop.

Hence, an apparatus that could automatically scan the eye (or other organ) in a steady and consistent manner is desired using one or more different types of ultrasonic probes, which will then provide improved images and hence provide a better final result. This device would ensure that the ultrasonic imaging probe is moved at a constant, regular rate, and may operate with a number of different types of probes as desired to broaden its applicability.

A secondary inaccuracy for the 3D model deals with alignment. The volumetric rendering algorithm naturally accounts for small misalignments when smoothing out frame to frame. However, if faced with a large wobble between pictures, it will still smooth out the frame, unknowing of the distorted volume it will create. Therefore, each image needs to be aligned to a landmark before it is made into a 3D model, or one image frame can be aligned to the adjacent image frame. Again, for the purposes of this example, any images that were irreconcilably skewed might be discarded. However, this can be improved by providing an alignment algorithm that will set all images in a certain landmark. A specialized machine can also help with this process.

For the example approach, the entire process from importing the original video, process all the images, and then creating the 3D model, advantageously takes only about 10-15 minutes. This varies depending on how many images need to be thrown out. This can be improved by using the specialized imaging machine, and additional improvements such as using the alignment algorithm.

Figure 5:
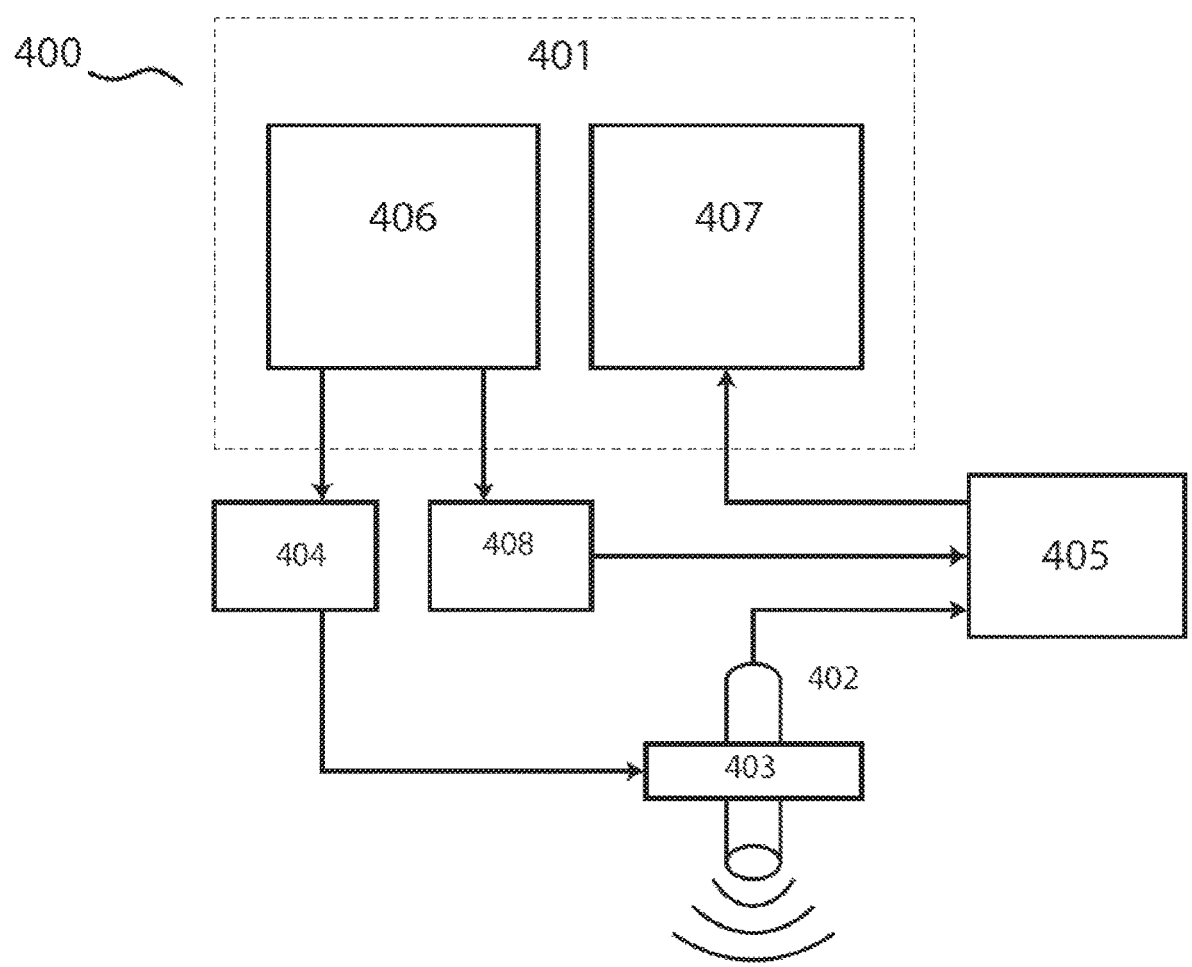
FIG. 5 is a schematic illustration of an example apparatus for collecting raw frames in a controlled and consistent fashion.

The example apparatus 400, schematically illustrated in FIG. 5 and described herein, will make obtaining such images a substantially easier process. This in turn will revolutionize performing and interpreting B-scan ultrasonography in ophthalmology and will eliminate the need for a very experienced ultrasonographer to be present to achieve the required and aspired best images in ocular ultrasonography.

The example apparatus 400 includes an ultrasound probe 402, a motor 403 connected to a motor controller 404 that powers and controls the movement of the probe, and sends the obtained digitized images to the connected computer 401 for further processing.

Image acquisition may be performed by an Aviso™ 50 MHz Ultrasound Biomicroscopy (UBM) probe, such as UBM probes from Quantel Medical, for example. The probe 402 rasters across the field of view capturing approximately ten frames per second.

The probe 402 may be attached to an Aviso™ module which powers and controls the probe 402, and sends the digitized information to a connected computer 401. The computer 401 stores the image sequences digitally in a proprietary Cineloop format, and can export them as AVI or JPEG formats.

Communication with the probe 402 uses the probe manufacturer's proprietary software, whereas customized software or open source software is utilized to control and/or communicate with the scanning machine. Commercially available software, customized software, and/or open source software can be utilized to process the resulting images, such as to practice a process such as described above.

The probe may be attached to a 2" (or about 5 cm) linear translation stage, such as stage model MTS50-Z8 provided from Thor labs, for example. The stage can achieve a 1.6-micron positional repeatability and ±0.25 mm/sec velocity stability. The stage is mechanically attached to a surgical microscope, such as a Leica surgical microscope, for example, which provides stability as well as a foot-controlled mechanical positioning.

Figure 6:
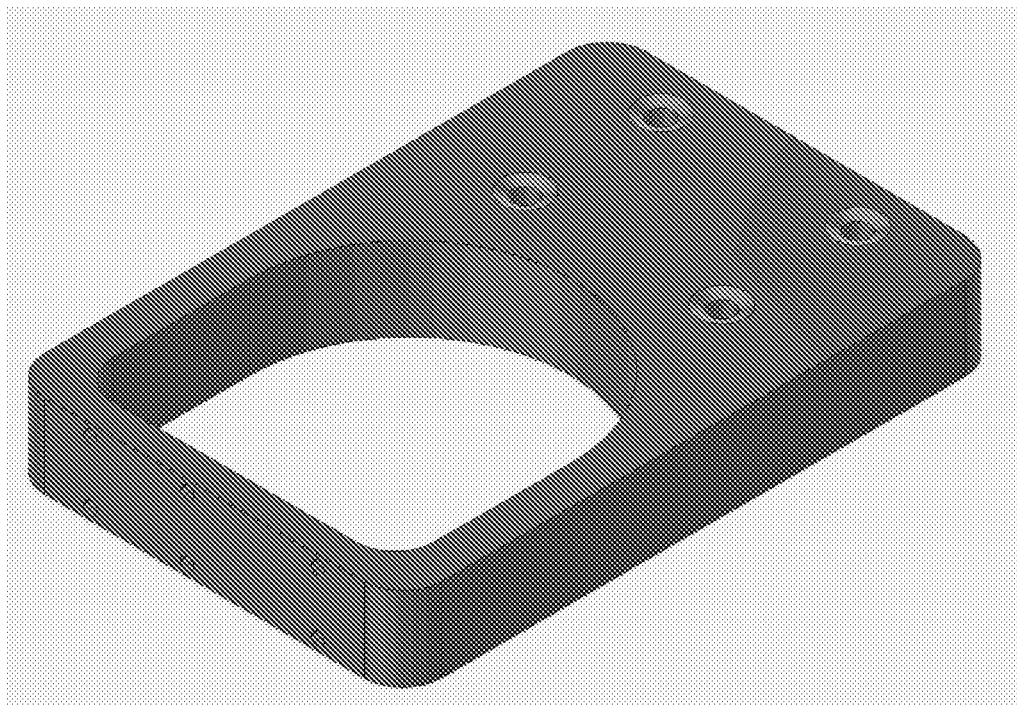
FIG. 6 is a perspective view of an example adapter which attaches the translation stage to the surgical microscope.

In one embodiment, the probe can be attached to the motor with an adapter (shown in FIG. 6), which is permanently fixed to the threaded holes on the translation stage and attaches the translation stage to the surgical microscope. It utilizes the threaded holes on the underside of the microscope head which are provided for attaching manufacturer-provided accessories. The adapter grips the probe like a vice and is tightened with two thumb screws. The motor may be attached to the microscope via a second adapter which utilizes the threaded holes on the fixed part of the translation stage and the adapter holes on the bottom of the microscope. In one embodiment, the adapter may be a 3D printed adapter.

Figure 7:
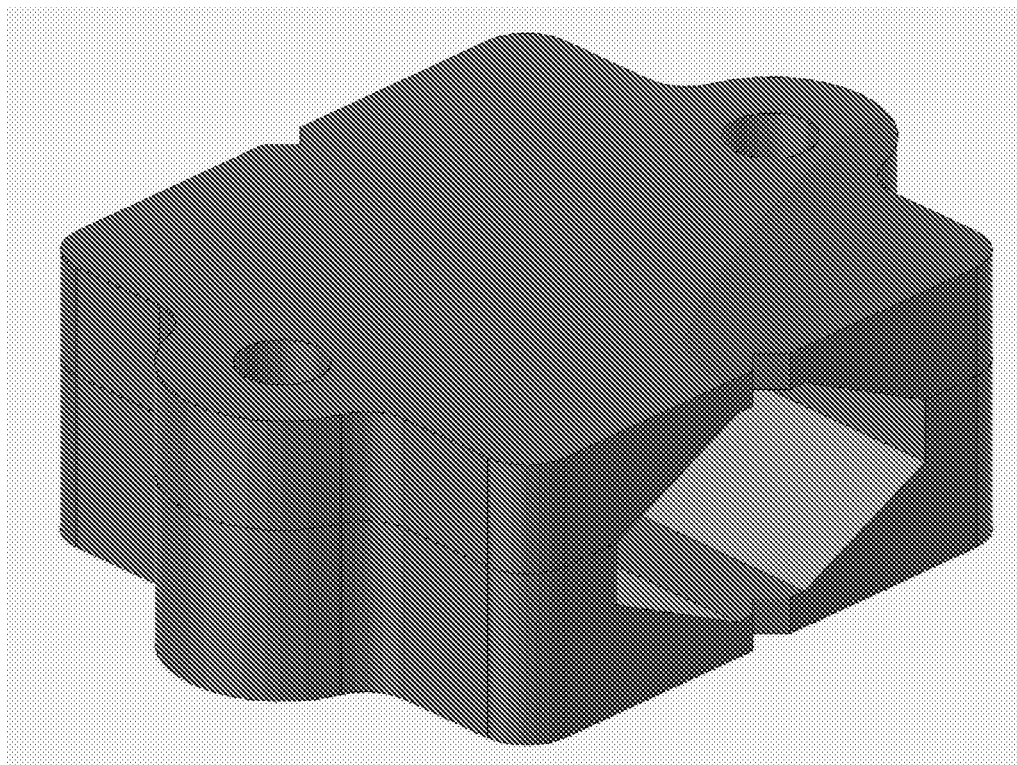
FIG. 7 is a perspective view of an example probe holder.

As further illustrated in FIG. 7, a probe holder can attach to the mobile part of the translation stage and can grip the probe handle, holding it parallel to the microscope's optical axis. The combination of the two adapters shown in FIG. 6 and FIG. 7 allows the probe to be positioned using the microscope's own controls. In one embodiment, the probe holder may be a 3D printed probe holder.

The motor can be controlled via a Thorlabs DC servo controller which can attach to the computer via a USB port. The controller allows either a crude manual positioning of the motor via a toggle switch or a precise control through the computer interface.

For automatic operation, the probe is turned on and off via a Numato single-channel USB relay 408 connected to the foot pedal port on the Aviso™ module. The relay 408 is wired such that the pedal remains operational.

Both the relay 408 and the motor controller 404 are connected to the same computer 401 running the Aviso™ software 407. The computer 401 runs a second, custom program 406 written in Python which coordinates the probe 402 motion with the probe data acquisition. This second custom program 406 allows the user to specify a region of the eye for data acquisition and the number of frames to be captured.

In manual operation, the probe is typically designed to be turned on and off by a foot pedal. The software provided by the manufacturer allows the user to capture a sequence of 2D images in the form of a multi-frame movie.

In one embodiment, the number of frames may be limited to cap the resolution in the swept direction to a certain number of pixels. In this embodiment, the approach would be to take several movies over smaller regions of the eye and combining the movies once the data acquisition is completed. Therefore, the start of a movie must be synchronized with the motion of the stage which can be accomplished by replacing the foot pedal with a computer-controlled relay from Numato lab. Wiring to the probe interface required the construction of a simple custom cable.

The stage is controlled by software prepared using Python. In one embodiment, the method may use as an input the starting and ending position of the stage and the number of segments into which that range should be divided. The method then may calculate the starting and stopping position of each division, add a little margin for stage acceleration, and ultimately compute the speed at which the stage must move to cover each division in exactly ten seconds (or whatever amount of time corresponds to one video recorded by the probe software). As the method may start and stop the stage on each pass, it may turn the probe on and off by toggling the relay.

In one embodiment, the ultrasonic probe may be seated on an immersion cup and may be thereby attached to the motor system.

In an embodiment, 3D reconstruction may be facilitated by intraocular contrast agents, such as lipid-bound fluorocarbon micro- and nano-bubbles. These agents may be injected into the anterior chamber to highlight structures, such as, but not limited to, the AC volume itself and the aqueous outflow pathway, including Schlemm's canal. The agents may also be used for making dynamic measurements, such as the aqueous outflow facility.

Alternative Image Reconstruction Methodology

As an additional approach, after the ultrasound video is isolated into individual frames, using basic image analysis techniques, to each frame is applied a filter, such as a Sobel filter, a Canny filter, a binary filter, or another process, to outline the edges of the structure. Next, the object outlined by the filter is filled in to create a binary gradient image. Finally, each frame is stacked together, given a depth, and is applied contour analysis to smooth out the overall three-dimensional object.

This approach can utilize different methods of processing the 2D images before reconstruction, such as image segmentation and manual binarization, or some other process. The processes are used to achieve the goal of creating a binary image. Different methods can be used for training and familiarity with the concepts, and to provide alternative solutions. For image segmentation, a filter is applied to each frame of the video that will allow the computer to sense the edges of the object of interest. Then the edges are filled in using cell detection algorithms to create a solid blob that outlines the object. For manual binarization, a histogram of the colors is created for a random image. Then, the low and high thresholds are determined through sliders. Values outside of the thresholds are black, the ones inside are white. The same two thresholds can be used for all consequent images. Finally, all of the images are stacked together and form a three dimensional model. This can be done using a commercial package such as Mathematica, ImageJ, or the Matlab® commercial package, or using customized software, for example. This program can be provided in the mobile realm using a customized application, such as using coding as a JavaScript package or a more complex and complete application.

The program processes the images in two different ways, both aiming for the same result. Image segmentation outlines the structure of the tissues using image segmentation algorithms as seen in the Matlab® commercial package online toolbox. Image segmentation for this example approach runs in six steps: importing the images, applying filters for edge detection, dilating the image, filling the interior gaps, removing connected objects on border, and finally smooth out the object.

After image segmentation is complete, contour analysis is applied as prescribed in the Matlab® commercial package toolbox to align each image along a landmark (e.g., the bottom of the iris) and then stack them together to reconstruct a three dimensional model. Details outlining the specifics of each step will appear in the following paragraphs. For illustrative and procedural purposes, the figures provided for the example process are all of cells and not of an eye, but the basic technique remains the same.

Importing the Images

The ultrasound video can include an arbitrary number of frames, which can be imported as a whole into a temporary working folder. The video may then be converted into a number of individual images corresponding to the number of frames, and the individual images can be saved in the same folder using the VideoReader and imwrite functions provided in the Matlab® commercial package, for example.

In one embodiment, for the example, the ultrasound video may include 100 frames and the video can be converted into 100 individual images and saved in the same folder using the VideoReader and imwrite functions provided in the Matlab® commercial package, for example.

Applying Sobel and Canny Filters

Sobel and Canny are both edge detection filters that utilize 2D spatial gradient measurements to create a binary image. Edge detection refers to the process of identifying and locating sharp discontinuities in an image. The discontinuities are abrupt changes in pixel intensity which characterize boundaries of objects in a scene. Edges in images are areas with strong intensity contrasts. Edge detecting an image significantly reduces the amount of data and filters out useless information, while preserving the important structural properties in an image. While the Matlab® commercial package has both filters as a built in function, for the purposes of example custom functions have been provided.

Dilating the Image

The binary gradient image shows lines of high contrast that indicate the edges of the object. These lines do not quite delineate the outline of the object of interest and gaps can be seen in the lines surrounding the object in the gradient mask. These linear gaps will disappear if the Sobel filter image is dilated using linear structuring elements, which can be created with the strel function. The binary gradient mask is dilated using the vertical structuring element followed by the horizontal structuring element.

Filling the Interior Gaps

The dilated gradient mask can show the outline of the object appropriately, but there may still be holes in the interior of the object. To fill these holes, the imfill function may be used.

Removing Connected Objects on the Border

The object of interest has been successfully segmented, but it is not the only object that has been found. Any objects that are connected to the border of the image can be removed using the imclearborder function. The connectivity in the imclearborder function was set to 4 to remove diagonal connections.

Smooth Out the Object

Furthermore, in order to make the segmented object look natural, the object is smoothed by eroding the image twice with a diamond structuring element. The diamond structuring element is created using the strel or bwperim function. The final product is a noise free binary image.

For manual binarization there are a total of 5 steps; conversion to grayscale, selecting a representative picture, creating a histogram of the values of each shade, finding the minimum and maximum thresholds, and finally creating the binary image. Note that although the manual process is described for the purpose of highlighting the process, such procedures are automated in the final procedure.

Converting to Grayscale

The function which converts the ultrasound video to individual frames saves each image as a RBG, rather than a grayscale. These images are processed as a grayscale image because of the interest in creating a binary image.

Selecting a Representative Image

For the example approach only about half of the images from the ultrasound may be used. Since the scan takes a period of 10 seconds to complete, usually more than one scan of different parts of the eye is performed in multiple segments, and more than one image is obtained. Any incomplete images are automatically thrown out. Additionally, thrown out are any images that may have been corrupted due to errors in transferring data. From the collection of images that remain, the first one is selected to determine the thresholds.

Creating a Historgram

A grayscale image is represented with number ranging from 0 to 100, with 0 being pure black and 100 being pure white. By creating a histogram of the values for each individual pixel, it can be seen which values make up the area of interest. The histogram is made with the function imhist. The histogram will then be used in the following step.

Finding Thresholds

Here is manually selected the thresholds for a binary filter. These thresholds will be applied to all the other images in the collection. The program will prompt an interactive GUI with the original monochrome image, the masked image outside the thresholds, and the final binarized image. There are interactive sliders that correspond to values on the histogram where the user can manually change the thresholds in real time to see the final binary image.

Creating the Binary Image

The thresholds represent the window of values of interest. The images are taken as an array of their individual grayscale values. Everything within the thresholds is changed to 1, and everything outside those values is changed to 0. The end result is the original picture being converted into a binary one. As an example, after the interactive GUI is complete, it will bring up a number of masked images corresponding to different imaging analysis techniques. These may not be used later on in the project, but may be useful for training purposes.

The final step is the conversion into 3D. As described above, this is done by creating an object that contains a three-dimensional array of values (or lists of values) that represent a 3D raster image. The first three dimensions of the object correspond to slices, rows, and columns, respectively. Slices are enumerated from top to bottom, rows from back to front, and columns from left to right. Then a 3D object is visualized using a set of techniques collectively known as volume rendering that display a projection of discretely sampled 3D data values. Given an object containing a regular volumetric grid, each volume element is known as a voxel and is represented by a single value (or list of values). Upon output, a 3D image formats as a picture of a projection of the image (not as a 3D array of values).

Results

As mentioned previously, one goal of this approach is to provide basic image enhancement techniques and image analysis techniques to produce the 2D to 3D ultrasound converter. All the steps listed in the methodology have been provided in a working example.

That being said, while the code functions correctly, the Sobel and Canny filters do not optimally outline the edges of the eye due to lack of contrast between the bright and dark parts. This is a problem with the main source of obtaining the video. The ultrasound does produce higher contrast videos, but at the cost of a drastic increase in background noise. The contours of interest, the iris, cornea, and sclera, appear too grainy and grey from the ultrasound video to properly outline using regular 2D spatial gradient algorithm.

The complete binarized image is better provided with better filters. However, with regards to the image segmentation analysis, each step is in working order.

The last and most important step is the actual creation of the 3D model. Simply put, each binary image is stacked in a 3D array along the z-direction. The images are then aligned and stabilized along the lens of the eye. Then through volume rendering algorithms, the gap between each corresponding white tile is smoothened while all black tiles are left as a blank space. The algorithm runs in all 3 planes to correct any abnormalities that occur if done in only one direction. Both the alignment and volumetric rendering algorithms are predetermined functions available through Mathematica. The resulting volume can be manipulated in the 3D space and the entire object can be rotated 360 degrees in any direction. Any ridges and deformation can be clearly seen in a 3D setting, compared to the original 2D images.

Discussion

The overall results of the method are in line with the main goal of the project. A 3D model of an eye was successfully created from an ultrasound video of that eye. This is a significant achievement in a revolutionary diagnostic tool. However, there are a number of improvements to be provided in additional examples. Firstly, the application of the Canny and Sobel filters can be improved upon. A fundamental problem with the way these filters worked impeded progress. Recall that both Canny and Sobel filters are edge detecting filters. They operate by discerning color gradients in the image and then map out a gradient with a drastic change. None of the gradients were large enough to detect major changes. The ultrasound produces a grayscale image that, by definition, is only shades of black and white. Without a large RBG color gradient to discern edges, the filter becomes less useful. For this reason a manual binarization program to accurately produce the binary images was used. Using a color image as a starting point could also improve the process.

Nevertheless, the resulting 3D model is workable, and the very first step in developing a high resolution model. While it does portray the acute deformations of the eye, it is still inaccurate to a certain degree. About half of images were thrown out before the final collection due to incomplete scans, distorted images, or images that were too blurry to use. In order to increase the resolution of the 3D model, ideally all 100 frames of the ultrasound video would be of one single pass through the eye, and all such frames are utilized. The process can be improved by making sure that one pass lasts exactly 10 seconds, the length of time it takes to film 100 frames. This is difficult, because it requires an extremely steady hand to move the ultrasound probe at a constant speed just 1 inch in 10 seconds.

Many other example embodiments can be provided through various combinations of the above described features and specific embodiments. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method for creating a three-dimensional image of an object from a two-dimensional ultrasound video, the method comprising:
  acquiring a plurality of two-dimensional ultrasound images of the object;
  recording a plurality of videos based on the acquired two-dimensional ultrasound images, each of the plurality of videos comprising a plurality of frames;
  separating each of the plurality of frames;
  cropping each of the plurality of frames to isolate structures intended to be reconstructed;
  selecting a frame near a center of the object and rotating the selected frame to create a main horizontal landmark;
  aligning each of the plurality of frames to the main horizontal landmark; and
  stacking each of the aligned plurality of frames into a three-dimensional volume.

2. The method according to claim 1, further comprising:
  removing inter-frame jitter by aligning each of the plurality of frames relative to a previous frame of the plurality of frames.

3. The method according to claim 1, further comprising:
  reducing a noise of each of the plurality of frames.

4. The method according to claim 3, wherein the reducing the noise of each of the plurality of frames comprises low-pass filtering or median filtering.

5. The method according to claim 3, further comprising stacking each of the plurality of frames with reduced noise into a reduced noise three-dimensional volume by removing layers of the three-dimensional image.

6. The method according to claim 5, wherein the removing layers of the three-dimensional image is performed by using planes to exclude voxels outside of a cuboidal region specified by a user.

7. The method according to claim 1, wherein the object is a part of a human body.

8. The method according to claim 7, wherein the object is a human eye.

9. The method according to claim 8, wherein the plurality of two-dimensional ultrasound images are B-scan images of the human eye.

10. The method according to claim 1, wherein the acquiring a plurality of two-dimensional ultrasound images is performed by a Quantel ultrasonic biomicroscope or a B-scan probe.

11. The method according to claim 1, wherein each of the plurality of frames represents an individual slice of a particular segment of one of the two-dimensional ultrasound images in one dimension.

12. The method according to claim 1, wherein the cropping each of the plurality of frames comprises excluding extraneous parts of the images.

13. The method according to claim 1, wherein the selecting the frame near the center of the object and rotating the image rotates all other frames by the same amount.

14. A method for creating a three-dimensional image of an object from a two-dimensional ultrasound video, the method comprising:
    obtaining a plurality of two-dimensional ultrasound video images of the object, each of the plurality of two-dimensional ultrasound video images comprising a plurality of individual frames;
    isolating each of the plurality of individual frames from each of the plurality of two-dimensional ultrasound video images;
    individually processing each of the plurality of individual frames to improve their suitability for conversion, wherein the individually processing each of the plurality of individual frames comprises selecting an individual frame near a center of the object and rotating the individual frame to create a main horizontal landmark; and
    assembling together the individually processed plurality of individual frames to create the three-dimensional image of the object.

15. The method according to claim 14, wherein the assembling together the individually processed plurality of individual frames uses landmarks that identify common areas in the individually processed plurality of individual frames.

16. The method according to claim 14, wherein the assembling together the individually processed plurality of individual frames aligns each of the individually processed plurality of individual frames based on image boundaries in adjacent frames of the individually processed plurality of individual frames.

17. The method according to claim 14, wherein the assembling together the individually processed plurality of individual frames aligns each of the individually processed plurality of individual frames based on the main horizontal landmark.

18. The method according to claim 14, wherein the assembling together the individually processed plurality of individual frames comprises:
    creating an object that contains a three-dimensional array of values, the three-dimensional array of values corresponding to slices, rows, and columns, wherein the slices are enumerated from top to bottom, the rows from back to front, and the columns from left to right;
    visualizing the three-dimensional image of the object by using volume rendering that displays a projection of discretely sampled three-dimensional data values, wherein each volume element is represented by a single value or a list of values; and
    outputting a three-dimensional image format as a picture of a projection of the image.

* * * * *